US008735415B2

(12) United States Patent
Kompella et al.

(10) Patent No.: US 8,735,415 B2
(45) Date of Patent: May 27, 2014

(54) ACID ADDITION SALTS OF (3,5-BIS TRIFLUOROMETHYL)-N-[4-METHYL-3-(4-PYRIDIN-3YL-PYRIMIDIN-2YLAMINO)-PHENYL]-BENZAMIDE

(75) Inventors: Amala Kishan Kompella, Hyderabad (IN); Sreenivas Rachakonda, Hyderabad (IN); Bhujanga rao Adibhatla Kali Satya, Hyderabad (IN); Venkaiah Chowdary Nannapaneni, Hyderabad (IN)

(73) Assignee: Natco Pharma Limited, Hyderabad, Andhra Pradesh (IN)

( * ) Notice: Subject to any disclaimer, the term of this patent is extended or adjusted under 35 U.S.C. 154(b) by 91 days.

(21) Appl. No.: 13/289,762

(22) Filed: Nov. 4, 2011

(65) Prior Publication Data
US 2012/0077833 A1   Mar. 29, 2012

Related U.S. Application Data

(63) Continuation-in-part of application No. 13/053,908, filed on Mar. 22, 2011, now abandoned, which is a continuation-in-part of application No. 12/042,240, filed on Mar. 4, 2008, now Pat. No. 7,939,541, which is a continuation-in-part of application No. 11/714,565, filed on Mar. 5, 2007, now Pat. No. 7,910,598, which is a continuation-in-part of application No. PCT/IN2005/000243, filed on Jul. 19, 2005.

(30) Foreign Application Priority Data

Sep. 9, 2004   (IN) .............................. 908/CHE/2004

(51) Int. Cl.
C07D 401/04   (2006.01)
A61K 31/506   (2006.01)

(52) U.S. Cl.
USPC ........................................................ 514/275

(58) Field of Classification Search
USPC .......................................... 544/331; 514/275
See application file for complete search history.

(56) References Cited

U.S. PATENT DOCUMENTS

| 5,516,775 | A | 5/1996 | Zimmermann et al. |
| 7,910,598 | B2 | 3/2011 | Kompella et al. |
| 7,939,541 | B2 | 5/2011 | Kompella et al. |
| 8,183,253 | B2 | 5/2012 | Kompella et al. |
| 2011/0190328 | A1 | 8/2011 | Kompella et al. |

FOREIGN PATENT DOCUMENTS

| EP | 0 564 409 | 10/1993 |
| EP | 0 588 762 A1 | 3/1994 |
| WO | WO 95/09847 | 4/1995 |
| WO | WO 95/09851 | 4/1995 |
| WO | WO 95/09853 | 4/1995 |
| WO | WO 99/03854 | 1/1999 |
| WO | WO 99/15164 A | 4/1999 |
| WO | WO 02/22597 | 3/2002 |
| WO | WO 2004/029038 A | 4/2004 |
| WO | WO 2004/002963 A1 | 8/2004 |
| WO | WO 2004/018699 A1 | 12/2004 |
| WO | WO 2004/110452 A | 12/2004 |
| WO | WO 2006/027795 A1 | 3/2006 |
| WO | WO 2008/058037 A1 | 5/2008 |

OTHER PUBLICATIONS

Ogata et al. "Synthesis and Antiviral activity of sulphonamidobenzophenone oximes and sulphonamidobenzamides." Journal of Medicinal Chemistry. vol. 29, No. 3. 1986. pp. 417-423.
Zimmermann et al. "Potent and selective inhibitors of the Abl-kinase: Phenylaminopyrimidine (PAP) derivatives." Bioorganic and Medicinal Chemistry Letters. vol. 7, No. 2. 1997. pp. 187-192.
Schindler et al. "Structural mechanism for STI-571 inhibition of Abelson tyrosine kinase." Science. vol. 289, No. 5486. 2000. pp. 1938-1942.
Simone, Oncology: Introduction, Cecil Textbook of Medicine, 20$^{th}$ Edition, vol. 1 (1996): 1004-1010.
Gura, "Systems for identifying new drugs are often faulty, cancer models," Science (2007) 278 (5340): 1041-1042.
Johnson et al., "Relationships between drug activity in NCI preclinical in vitro and in vivo models and early clinical trials," British Journal of Cancer (2001) 64 (10): 1424-1431.
Examination Report from corresponding European Application No. 05 779 775.5-2101 dated Feb. 16, 2010.
Examination Report from corresponding European Application No. 05 779 775.5-2101 dated Apr. 25, 2008.
Invitation to Pay Additional Fees with Partial International Search mailed Jul. 15, 2009.
Hughes et al., "Cardiovascular activity of aromatic guanidine compounds," J. Med. Chem. (1975) 18 (11): 1077-1088. XP002960647.

(Continued)

Primary Examiner — Deepak Rao
(74) Attorney, Agent, or Firm — Merchant & Gould P.C.

(57) ABSTRACT

The present invention relates to acid addition salts of the pharmaceutically active compound (3,5-Bistrifluoromethyl)-N-[4-methyl-3-(4-pyridin-3yl-pyrimidin-2ylamino)-phenyl]-benzamide(I):

Formula -(I)

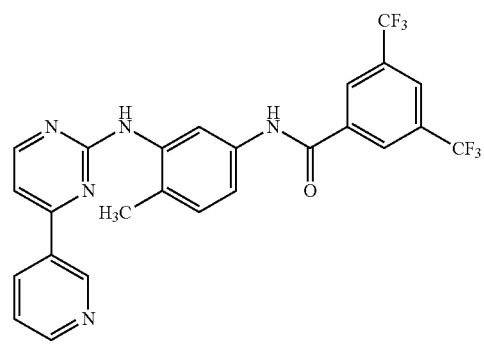

Development Code—AN019
The invention also relates to processes for the preparation these acid addition salts and to their use as anti tumor agent in humans.

11 Claims, 6 Drawing Sheets

(56) References Cited

OTHER PUBLICATIONS

Ogata et al., "Synthesis and antiviral activity of sulfonamidobenzophenone oximes and sulfonamidobenzamides," J. Med. Chem. (1986) 29: 417-423. XP002096176.

Communication from EPO with extended European Search Report for corresponding EP application No. 10 18 4904 mailed on Dec. 15, 2010.

Herrmann et al., "A rapid and simple method for the isolation of apoptotic DNA fragments," *Nucleic Acids Research* (1994) 22 (24): 5506-5507.

Okram et al., "A general strategy for creating 'Inactive-conformation' AbI inhibitors," *Chemistry & Biology* (2006) 13 (7): 779-786.

Okram et al., "Supplemental Data: A general strategy for creating 'Inactive-conformation' AbI inhibitors," *Chemistry & Biology* (2006) 13 (7): 1-24.

U.S. Office Action dated Oct. 4, 2012 cited in U.S. Appl. No. 13/053,908.

Adeyeye, Moji, ed., Preformulation in Solid Dosage Form Development (Informa Healthcare, 2008) Chapter 2.3, pp. 63-80.

Bastin et al., Organic Process Research & Development 2000, 4, 427-435.

Gould, International J. of Therapeutics 33, 201 (1986).

Liu, Rong, ed., Water-Insoluble Drug Formulation (CRC Press, 2008) Chapter 15 pp. 417-435.

Morris, et al., International Journal of Pharmaceutics 105 (1994) 209-217.

Pearce et al., Failure modes in anticancer drug discovery and development, Cancer Drug Design and Discovery Edited by Stephen Neidle, Chapter 18, pp. 424-435 (2008).

Serajuddin, Advanced Drug Delivery Reviews 59 (2007) 603-616.

Swarbrick et al., eds. Encyclopedia of Pharmaceutical Technology 13 (Marcel Dekker, NY 1996) pp. 453-499.

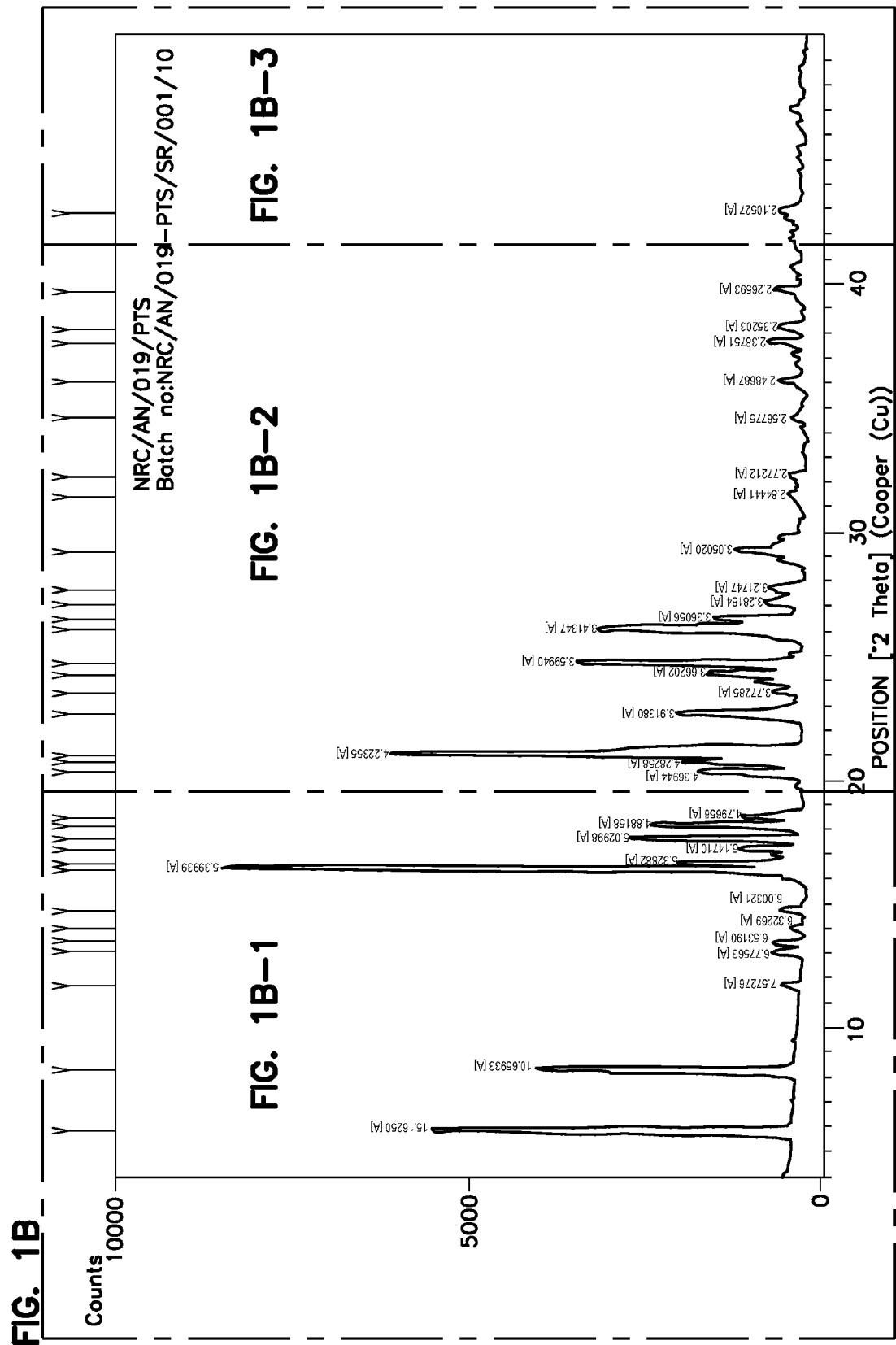

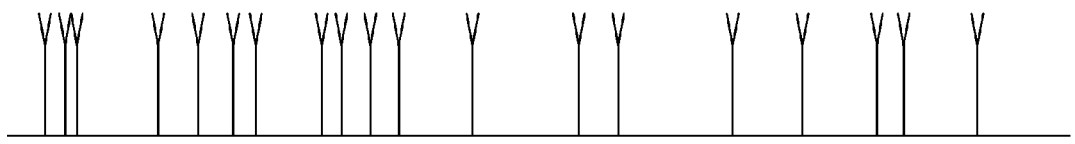
FIG. 1B-2
NRC/AN/019/PTS
Batch no:NRC/AN/019
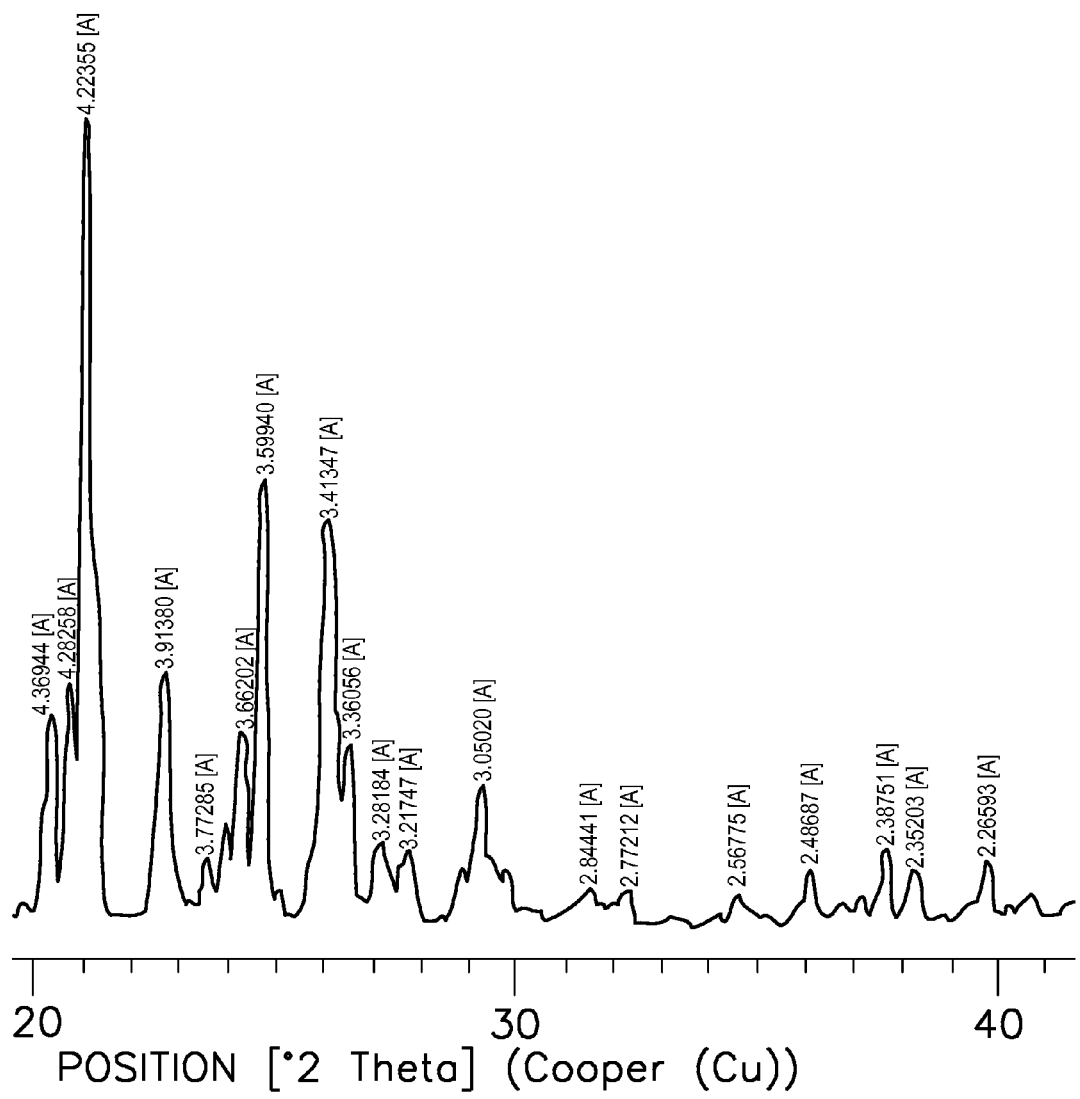

FIG. 2

Peak List

| Pos. [°2Th.] | Height [cts] | FWHM [°2TH] | d-spacing[A] | Rel. Int. [%] |
|---|---|---|---|---|
| 5.8241 | 5154.71 | 0.1560 | 15.16250 | 61.56 |
| 8.2882 | 3705.53 | 0.0936 | 10.65932 | 44.25 |
| 11.6764 | 220.10 | 0.1872 | 7.57276 | 2.63 |
| 13.0558 | 407.53 | 0.2496 | 6.77563 | 4.87 |
| 13.5452 | 432.43 | 0.1560 | 6.53190 | 5.16 |
| 13.9956 | 188.90 | 0.1872 | 6.32269 | 2.26 |
| 14.7444 | 373.73 | 0.1716 | 6.00321 | 4.46 |
| 16.4041 | 8373.23 | 0.1248 | 6.39939 | 100.00 |
| 16.6228 | 1805.88 | 0.1092 | 5.32882 | 21.57 |
| 17.2141 | 959.93 | 0.1404 | 5.14710 | 11.46 |
| 17.6181 | 2479.55 | 0.1092 | 5.02998 | 29.61 |
| 18.1581 | 2187.94 | 0.1716 | 4.88158 | 26.13 |
| 18.4828 | 906.11 | 0.1092 | 4.79656 | 10.82 |
| 20.3078 | 1497.52 | 0.1560 | 4.36944 | 17.88 |
| 20.7242 | 1704.60 | 0.1248 | 4.28256 | 20.36 |
| 21.0171 | 5927.63 | 0.0936 | 4.22355 | 70.79 |
| 22.7017 | 1808.96 | 0.1560 | 3.91380 | 21.60 |
| 23.5617 | 434.74 | 0.1560 | 3.77285 | 5.19 |
| 24.2855 | 1384.77 | 0.1560 | 3.66202 | 16.54 |
| 24.7146 | 3241.18 | 0.1092 | 3.59940 | 38.71 |
| 26.0839 | 2937.61 | 0.2496 | 3.41347 | 35.08 |
| 26.5020 | 1305.60 | 0.1716 | 3.36056 | 15.59 |
| 27.1497 | 573.99 | 0.3120 | 3.28184 | 6.86 |
| 27.7036 | 476.27 | 0.3120 | 3.21747 | 5.69 |
| 29.2557 | 979.34 | 0.1248 | 3.05020 | 11.70 |
| 31.4251 | 232.38 | 0.3744 | 2.84441 | 2.78 |
| 32.2667 | 250.22 | 0.2808 | 2.77212 | 2.99 |
| 34.6355 | 152.49 | 0.3744 | 2.58775 | 1.82 |
| 36.0878 | 397.55 | 0.1248 | 2.48687 | 4.75 |
| 37.6449 | 532.83 | 0.1248 | 2.38751 | 6.72 |
| 38.2346 | 404.70 | 0.1872 | 2.35203 | 4.83 |
| 39.7475 | 451.90 | 0.1248 | 2.26593 | 5.40 |
| 42.9248 | 367.27 | 0.3120 | 2.10527 | 4.39 |

ACID ADDITION SALTS OF (3,5-BIS TRIFLUOROMETHYL)-N-[4-METHYL-3-(4-PYRIDIN-3YL-PYRIMIDIN-2YLAMINO)-PHENYL]-BENZAMIDE

This application is a Continuation-In-Part of U.S. application Ser. No. 13/053,908, filed 22 Mar. 2011, which is a Continuation-in-Part of U.S. application Ser. No. 12/042,240, filed 4 Mar. 2008, which is a Continuation-in-Part of U.S. application Ser. No. 11/714,565 filed 5 Mar. 2007, which is a Continuation-in-Part of PCT/IN2005/000243 filed 19 Jul. 2005, which claims benefit of Serial No. 908/CHE/2004 filed 9 Sep. 2004 in India and which applications are incorporated herein by reference. A claim of priority to all, to the extent appropriate is made.

FIELD OF THE INVENTION

The present invention relates to acid addition salts of the pharmaceutically active compound (3,5-Bistrifluoromethyl)-N-[4-methyl-3-(4-pyridin-3-yl-pyrimidin-2-ylamino)-phenyl]-benzamide(I):

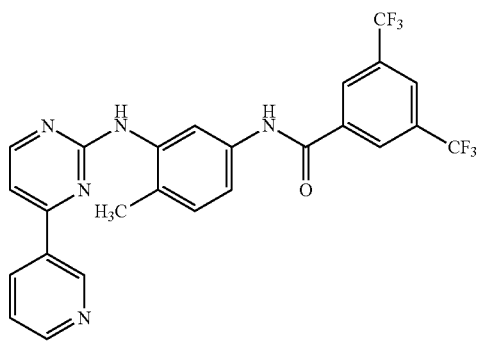 [SMILES: Cc1ccc(NC(=O)c2cc(C(F)(F)F)cc(C(F)(F)F)c2)cc1Nc1nccc(-c2cccnc2)n1]

Formula-(I)

Development Code—AN019

The invention also relates to processes for the preparation these acid addition salts and to their use as anti tumor agent in humans.

BACKGROUND OF THE INVENTION

The preparation of (3,5-Bis trifluoromethyl)-N-[4-methyl-3-(4-pyridin-3-yl-pyrimidin-2-ylamino)-phenyl]-benzamide of formula-I, and the use thereof, especially as an anti-tumor agent, are described in Examples 3 and 4 of WO2006/027795 (PCT/IN05/00243 filed Jul. 19, 2005, published 16 Mar. 2006) and in equivalent applications in numerous other countries including the USA (pub. No.: US 2007/0232633). The crystal forms of (3,5-Bis trifluoromethyl)-N-[4-methyl-3-(4-pyridin-3-yl-pyrimidin-2-ylamino)-phenyl]-benzamide of formula I are described in US2009227611. In these publications, acid addition salts are not discussed.

Basic pharmaceutical active compounds are commonly formulated into pharmaceutical preparations as an acid addition salt form, particularly as a crystalline acid addition salt. Although it is known that the preparation of salt forms may improve the physical or pharmaceutical properties of a basic pharmaceutical active compound, it is not possible to predict which salt forms may possess advantages for a particular purpose prior to the actual preparation and characterization of the salt form.

SUMMARY OF THE INVENTION

The present invention includes a compound of formula (II):

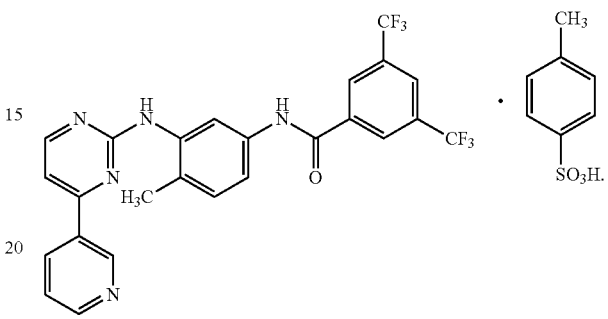

This compound can be identified by the chemical name (3,5-Bis trifluoromethyl)-N-[4-methyl-3-(4-pyridin-3-yl-pyrimidin-2-ylamino)-phenyl]-benzamide, 4-toluene sulfonate.

The present invention also includes a method of preparing a compound of formula (II):

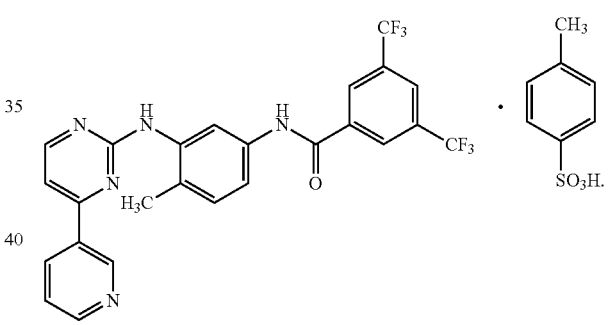

This method can include treating a compound of formula (I):

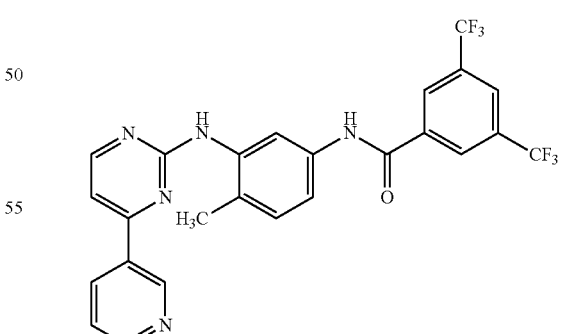

with 4-toluene sulfonic acid in methanol at room temperature.

The present invention also includes a method of treating chronic myelogenous leukemia in a subject in need thereof. This method can include administering to the subject an effective amount of a compound of formula II:

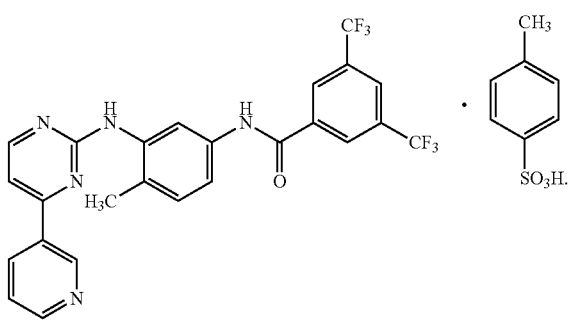 [SMILES: Cc1ccc(NC(=O)c2cc(C(F)(F)F)cc(C(F)(F)F)c2)cc1Nc1nccc(-c2cccnc2)n1 ; Cc1ccc(S(=O)(=O)O)cc1]

The present invention also includes a method of treating glioma, ovarian tumor, pancreatic tumor, tumor of the lung, tumor of the breast, or leukemia in a subject in need thereof. This method can include administering to the subject an effective amount of a compound of formula II, which is shown above.

The present invention also includes a salt of the compound (3,5-bis trifluoromethyl)-N-[4-methyl-3-(4-pyridin-3-yl-pyrimidin-2-ylamino)-phenyl]-benzamide; wherein the salt comprises an acid addition salt selected from the group consisting of hydrochloride, hydrobromide, sulphate, methane sulfonate, acetate, propionate, sulphate, phosphate, butyrate, oxalate, nicotinate, camphor sulfonate, para-toluene methane sulfonate, benzene sulfonate, trifluoro methane acetate, trifluoro sulfonate, stearate, and oleate. This salt can be employed in a method of treating a proliferative disorder in a subject in need thereof. This method can include administering to the subject an effective amount of the salt.

DETAILED DESCRIPTION OF THE INVENTION

Figure 1A:
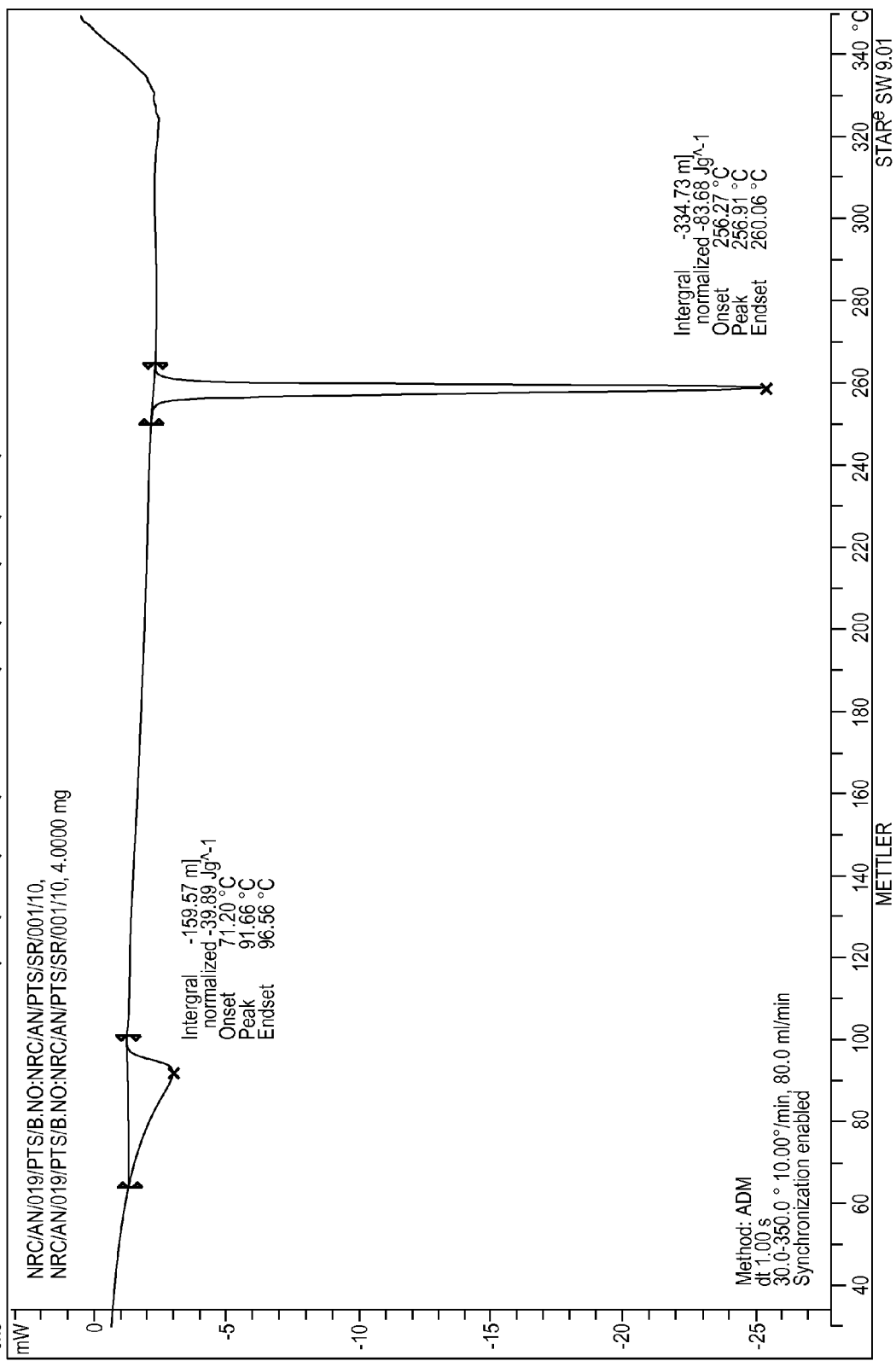
FIG. 1 illustrates the results of differential scanning calorimetry obtained for the tosylate salt of (3,5-Bis trifluoromethyl)-N-[4-methyl-3-(4-pyridin-3-yl-pyrimidin-2-ylamino)-phenyl]-benzamide.

The present invention relates to salt forms of (3,5-Bis trifluoromethyl)-N-[4-methyl-3-(4-pyridin-3-yl-pyrimidin-2-ylamino)-phenyl]-benzamide that are useful, for example, for the manufacture of solid or liquid pharmaceutical dosage forms. Suitable solid oral dosage forms include tablets and capsules. Suitable liquid oral dosage forms include orally administered solutions and suspensions. Other suitable dosage forms include suppositories and the like. Each of the present salt forms possesses one or more properties that provides advantages when used as a pharmaceutical active ingredient, such as physical properties that make it easier to manufacture one or more dosage forms, improved stability, improved bioavailability and other such properties.

In an embodiment, the salt form of the present invention includes (3,5-bis trifluoromethyl)-N-[4-methyl-3-(4-pyridin-3-yl-pyrimidin-2-ylamino)-phenyl]-benzamide acid addition salts selected from the group consisting of hydrochloride, hydrobromide, sulphate, methane sulfonate, acetate, propionate, sulphate, phosphate, butyrate, oxalate, nicotinate, camphor sulfonate, para-toluene methane sulfonate, benzene sulfonate, trifluoro methane acetate, trifluoro sulfonate, stearate, and oleate. In an embodiment, the salt form of the present invention includes (3,5-bis trifluoromethyl)-N-[4-methyl-3-(4-pyridin-3-yl-pyrimidin-2-ylamino)-phenyl]-benzamide acid addition salts such as tosylate, mesylate, or hydrochloride.

The inventors also surprisingly found that the acid addition salt form of (3,5-Bis trifluoromethyl)-N-[4-methyl-3-(4-pyridin-3-yl-pyrimidin-2-ylamino)-phenyl]-benzamide and "p-toluene sulfonic acid" provides the advantages considerably high solubility, low hygroscopicity, and good flow properties, which make it suitable for use in dosage forms. (3,5-Bis trifluoromethyl)-N-[4-methyl-3-(4-pyridin-3-yl-pyrimidin-2-ylamino)-phenyl]-benzamide tosylate salt has the following general formula (II):

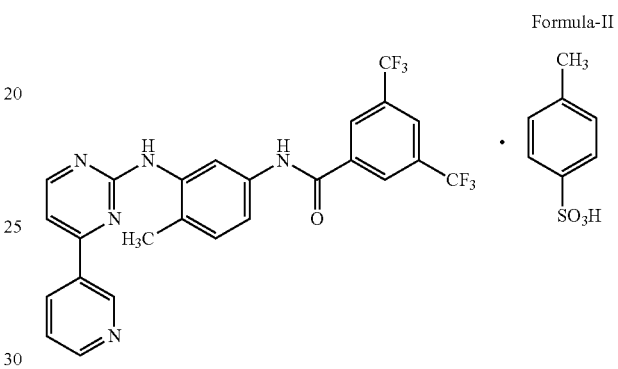

Formula-II

The salt forms of (3,5-Bis trifluoromethyl)-N-[4-methyl-3-(4-pyridin-3-yl-pyrimidin-2-ylamino)-phenyl]-benzamide can be prepared by known methods for making acid addition salts of amines, e.g., by treatment with an acid or a suitable anion exchange reagent. For example, (3,5-Bis trifluoromethyl)-N-[4-methyl-3-(4-pyridin-3-yl-pyrimidin-2-ylamino)-phenyl]-benzamide or a solution of (3,5-Bis trifluoromethyl)-N-[4-methyl-3-(4-pyridin-3yl-pyrimidin-2-ylamino)-phenyl]-benzamide can be combined with a solution of an organic or mineral acid in, e.g., an alcohol (such as methanol, isopropanol, or butanol) with or without heating. The salt can be isolated by crystallization or by evaporation of the solvent and, if desired, purified by re-crystallization from an appropriate re-crystallization solvent by known methods.

For the purpose of administering a salt of (3,5-Bis trifluoromethyl)-N-[4-methyl-3-(4-pyridin-3-yl-pyrimidin-2-ylamino)-phenyl]-benzamide by means of an oral solution, those salts that have an increased water solubility compared to the free base can be advantageous. Salts having a lower water solubility compared to the free base can be more suitable for the manufacture of sustained release formulations.

The invention also relates to a method of treating warm-blooded animals suffering from a tumor disease including administering a predetermined dose of the tosylate addition salt of (3,5-Bis trifluoromethyl)-N-[4-methyl-3-(4-pyridin-3-yl-pyrimidin-2-ylamino)-phenyl]-benzamide effective against the disease concerned. The p-toluene sulfonate salt (II) of the present invention exhibits anti-proliferative and tumor inhibiting activity and can be administered to warm-blooded animals in need of such treatment. The p-toluene sulfonate salt (II) of the present invention can be administered for treating gliomas, ovarian tumors, pancreatic tumors, tumors of the lung (e.g., small cell lung carcinoma), tumors of the breast, and leukemia. In an embodiment, the p-toluene sulfonate salt (II) of the present invention can be administered for treating leukemia.

In an embodiment, the present invention includes a compound of formula (II):

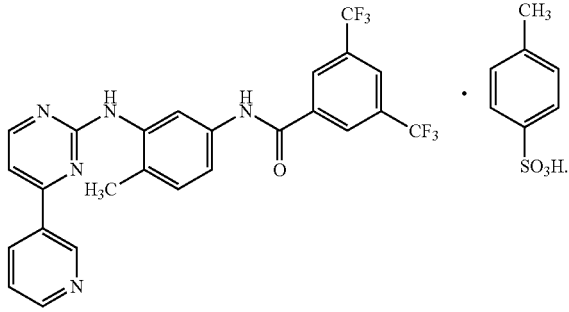 [SMILES: Cc1ccc(NC(=O)c2cc(C(F)(F)F)cc(C(F)(F)F)c2)cc1Nc1nccc(-c2cccnc2)n1 ; Cc1ccc(S(=O)(=O)O)cc1]

This compound of formula II has the chemical name (3,5-Bis trifluoromethyl)-N-[4-methyl-3-(4-pyridin-3-yl-pyrimidin-2-ylamino)-phenyl]-benzamide, 4-toluene sulfonate. In an embodiment, this compound can remain essentially non hygroscopic at the relative humidity of 75% and at 45° C. In an embodiment, this compound has powder x-ray diffraction (PXRD) characteristics as depicted in FIG. 2. Table A below provides a peak list corresponding to the diffractogram shown in FIG. 2.

| Pos.[°2Th.] | Height[cts] | FWHM[°2Th.] | d-spacing[Å] | Rel.Int.[%] |
|---|---|---|---|---|
| 5.8241 | 5154.71 | 0.1560 | 15.16250 | 61.56 |
| 8.2882 | 3705.53 | 0.0936 | 10.65932 | 44.25 |
| 11.6764 | 220.10 | 0.1872 | 7.57276 | 2.63 |
| 13.0558 | 407.53 | 0.2496 | 6.77563 | 4.87 |
| 13.5452 | 432.43 | 0.1560 | 6.53190 | 5.16 |
| 13.9956 | 188.90 | 0.1872 | 6.32269 | 2.26 |
| 14.7444 | 373.73 | 0.1716 | 6.00321 | 4.46 |
| 16.4041 | 8373.23 | 0.1248 | 5.39939 | 100.00 |
| 16.6228 | 1805.88 | 0.1092 | 5.32882 | 21.57 |
| 17.2141 | 959.93 | 0.1404 | 5.14710 | 11.46 |
| 17.6181 | 2479.55 | 0.1092 | 5.02998 | 29.61 |
| 18.1581 | 2187.94 | 0.1716 | 4.88158 | 26.13 |
| 18.4828 | 906.11 | 0.1092 | 4.79656 | 10.82 |
| 20.3078 | 1497.52 | 0.1560 | 4.36944 | 17.88 |
| 20.7242 | 1704.60 | 0.1248 | 4.28256 | 20.36 |
| 21.0171 | 5927.63 | 0.0936 | 4.22355 | 70.79 |
| 22.7017 | 1808.96 | 0.1560 | 3.91380 | 21.60 |
| 23.5617 | 434.74 | 0.1560 | 3.77285 | 5.19 |
| 24.2855 | 1384.77 | 0.1560 | 3.66202 | 16.54 |
| 24.7146 | 3241.18 | 0.1092 | 3.59940 | 38.71 |
| 26.0839 | 2937.61 | 0.2496 | 3.41347 | 35.08 |
| 26.5020 | 1305.60 | 0.1716 | 3.36056 | 15.59 |
| 27.1497 | 573.99 | 0.3120 | 3.28184 | 6.86 |
| 27.7036 | 476.27 | 0.3120 | 3.21747 | 5.69 |
| 29.2557 | 979.34 | 0.1248 | 3.05020 | 11.70 |
| 31.4251 | 232.38 | 0.3744 | 2.84441 | 2.78 |
| 32.2667 | 250.22 | 0.2808 | 2.77212 | 2.99 |
| 34.6355 | 152.49 | 0.3744 | 2.58775 | 1.82 |
| 36.0878 | 397.55 | 0.1248 | 2.48687 | 4.75 |
| 37.6449 | 562.83 | 0.1248 | 2.38751 | 6.72 |
| 38.2346 | 404.70 | 0.1872 | 2.35203 | 4.83 |
| 39.7475 | 451.90 | 0.1248 | 2.26593 | 5.40 |
| 42.9248 | 367.27 | 0.3120 | 2.10527 | 4.39 |

In an embodiment, this compound has anti-proliferative properties against the cell lines K562 and T315I. In an embodiment, this compound is effective for treating a subject suffering from chronic myelogenous leukemia.

The present invention also includes a method of preparing a compound of formula (II):

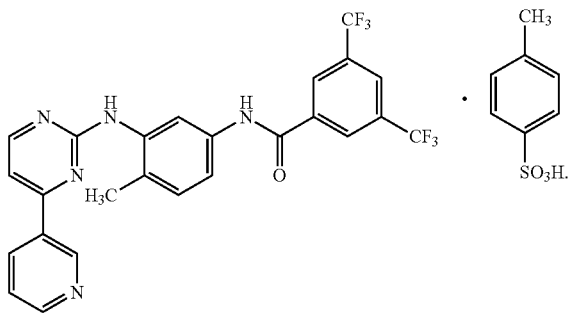 [SMILES: Cc1ccc(NC(=O)c2cc(C(F)(F)F)cc(C(F)(F)F)c2)cc1Nc1nccc(-c2cccnc2)n1 ; Cc1ccc(S(=O)(=O)O)cc1]

This method can include treating a compound of formula (I):

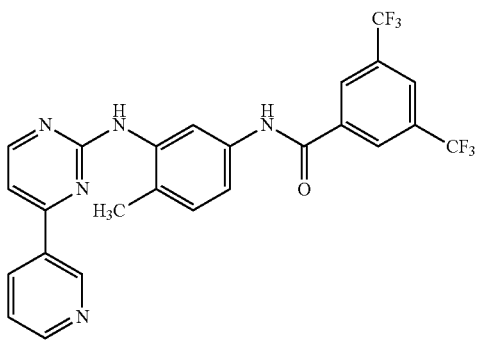 [SMILES: Cc1ccc(NC(=O)c2cc(C(F)(F)F)cc(C(F)(F)F)c2)cc1Nc1nccc(-c2cccnc2)n1]

with 4-toluene sulfonic acid in methanol at room temperature.

The present invention also includes a method of treating chronic myelogenous leukemia in a subject in need thereof. This method includes administering to the subject an effective amount of a compound of formula II:

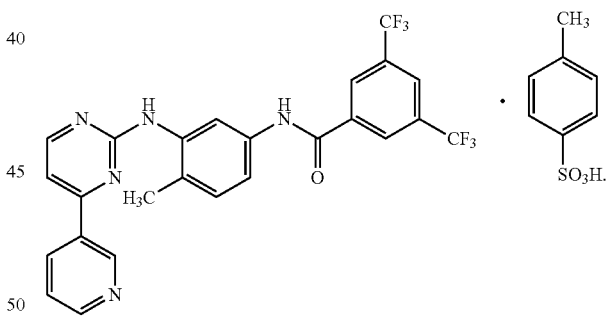

In an embodiment the compound of Formula (II) can be employed in a method of treating glioma, ovarian tumor, pancreatic tumor, tumor of the lung, tumor of the breast, or leukemia in a subject in need thereof. This embodiment includes administering to the subject an effective amount of a compound of formula II.

In an embodiment, the present invention includes a method of treating a proliferative disorder in a subject in need thereof. This embodiment includes administering to the subject an effective amount of a salt of the compound (3,5-bis trifluoromethyl)-N-[4-methyl-3-(4-pyridin-3-yl-pyrimidin-2-ylamino)-phenyl]-benzamide; wherein the salt comprises an acid addition salt selected from the group consisting of hydrochloride, hydrobromide, sulphate, methane sulfonate, acetate, propionate, sulphate, phosphate, butyrate, oxalate, nicotinate, camphor sulfonate, para-toluene methane sulfonate, benzene sulfonate, trifluoro methane acetate, trifluoro sulfonate, stearate, and oleate. In an embodiment, the acid addition salt includes or is tosylate, mesylate, or hydrochloride. In an embodiment, the acid addition salt includes or is tosylate. In an embodiment, the proliferative disorder includes or is chronic myelogenous leukemia. In an embodiment, the proliferative disorder includes or is a tumor.

The present invention may be better understood with reference to the following examples. These examples are intended to be representative of specific embodiments of the invention, and are not intended as limiting the scope of the invention.

EXAMPLES

Example-1

(3,5-Bis trifluoromethyl)-N-[4-methyl-3-(4-pyridin-3-yl-pyrimidin-2-ylamino)-phenyl]-benzamide hydrochloride Aqueous hydrochloric acid (1.06 g of 37%) was added to a refluxing solution of (3,5-Bis trifluoromethyl)-N-[4-methyl-3-(4-pyridin-3-yl-pyrimidin-2-ylamino)-phenyl]-benzamide (5 g, 0.0096 moles) in n-butanol (150 ml). The clear solution was brought to room temperature and maintained under stirring for 2 hours. The separated product was filtered-off and dried to yield (3,5-Bis trifluoromethyl)-N-[4-methyl-3-(4-pyridin-3-yl-pyrimidin-2-ylamino)-phenyl]-benzamide hydrochloride as a pale-yellow crystalline solid having the following analytical properties:
Moisture content by Karl-Fischer method: 0.6% (wt/wt)
HCl content: 6.4%
Melting range: 235-245° C.

Example-2

(3,5-Bis trifluoromethyl)-N-[4-methyl-3-(4-pyridin-3-yl-pyrimidin-2-ylamino)-phenyl]-benzamide methane sulfonate Methane sulfonic acid (1.85 g, 0.0193 moles) was added to a suspension of (3,5-Bis trifluoromethyl)-N-[4-methyl-3-(4-pyridin-3-yl-pyrimidin-2-ylamino)-phenyl]-benzamide (10 g, 0.0193 moles) in methanol (110 ml) at room temperature. To the clear solution isopropyl alcohol (30 ml) was added and stirred at room temperature for 3 hours. The precipitated (3,5-Bis trifluoromethyl)-N-[4-methyl-3-(4-pyridin-3-yl-pyrimidin-2-ylamino)-phenyl]-benzamide mesylate was filtered and dried to afford a pale-yellow crystalline solid having the following analytical properties:
Moisture content by Karl-Fischer method: 0.6% (wt/wt)
Melting range: 224-227° C.

Example-3

(3,5-Bis trifluoromethyl)-N-[4-methyl-3-(4-pyridin-3-yl-pyrimidin-2-ylamino)-phenyl]-benzamide 4-toluene sulfonate monohydrate p-Toluene sulfonic acid (7.35 g, 0.0386 moles) was added to a suspension of (3,5-Bis trifluoromethyl)-N-[4-methyl-3-(4-pyridin-3-yl-pyrimidin-2-ylamino)-phenyl]-benzamide (20 g, 0.0386 moles) in methanol (400 ml) at room temperature. The solution was refluxed for 30 minutes and brought to room temperature. The crystallized (3,5-Bis trifluoromethyl)-N-[4-methyl-3-(4-pyridin-3-yl-pyrimidin-2-ylamino)-phenyl]-benzamide 4-toluene sulfonate was filtered and dried to afford a yellow crystalline solid having the following analytical properties:
Moisture content by Karl-Fischer method: 2.7% (wt/wt)
Melting range: 255-258° C.

Example-4

Stability Under High Humidity Conditions

For illustration of the non-hygroscopic nature of the (3,5-Bis trifluoromethyl)-N-[4-methyl-3-(4-pyridin-3-yl-pyrimidin-2-ylamino)-phenyl]-benzamide hydrochloride, mesylate, and tosylate salts, these salts were kept in stability chambers and their water contents were determined by Karl-Fischer method. The results are tabulated below.

TABLE 1

| Sample | Initial moisture content (%) | Final moisture content - After 48 hours at 25° C. at humidity of 60% | Final moisture content - After 48 hours at 40° C. at humidity of 75% |
| --- | --- | --- | --- |
| (3,5-Bis trifluoromethyl)-N-[4-methyl-3-(4-pyridin-3yl-pyrimidin-2ylamino)-phenyl]-benzamide hydrochloride | 0.6% | 0.7% | 0.7% |
| (3,5-Bis trifluoromethyl)-N-[4-methyl-3-(4-pyridin-3yl-pyrimidin-2ylamino)-phenyl]-benzamide mesylate | 0.6% | 0.7% | 0.7% |
| (3,5-Bis trifluoromethyl)-N-[4-methyl-3-(4-pyridin-3yl-pyrimidin-2ylamino)-phenyl]-benzamide tosylate | 2.7% | 2.7% | 2.8% |

The above table shows that the hydrochloride, mesylate, and tosylate salts of (3,5-Bis trifluoromethyl)-N-[4-methyl-3-(4-pyridin-3-yl-pyrimidin-2-ylamino)-phenyl]-benzamide are non-hygroscopic and have substantial stability even under humidity conditions.

Example-5

Solubility

Solubility of (3,5-Bis trifluoromethyl)-N-[4-methyl-3-(4-pyridin-3-yl-pyrimidin-2-ylamino)-phenyl]-benzamide salts was determined by the shake flask method and the results obtained are shown below. General conditions: Room temperature (25° C.), stirring speed: 200 RPM, Analytical method: UV

TABLE 2

| Sample | Medium | Solubility (mg/ml) |
|---|---|---|
| (3,5-Bis trifluoromethyl)-N-[4-methyl-3-(4-pyridin-3yl-pyrimidin-2ylamino)-phenyl]-benzamide hydrochloride | Water<br>0.1N HCl | Almost no solubility<br>0.0134 |
| (3,5-Bis trifluoromethyl)-N-[4-methyl-3-(4-pyridin-3yl-pyrimidin-2ylamino)-phenyl]-benzamide mesylate | Water<br>0.1N HCl | 0.0014<br>0.03120 |
| (3,5-Bis trifluoromethyl)-N-[4-methyl-3-(4-pyridin-3yl-pyrimidin-2ylamino)-phenyl]-benzamide tosylate | Water<br>0.1N HCl | 0.0078<br>0.04020 |
| (3,5-Bis trifluoromethyl)-N-[4-methyl-3-(4-pyridin-3yl-pyrimidin-2ylamino)-phenyl]-benzamide (base) | Water<br>0.1N HCl | Almost no solubility<br>0.0013 |

Table-2 shows that (3,5-Bis trifluoromethyl)-N-[4-methyl-3-(4-pyridin-3yl-pyrimidin-2-ylamino)-phenyl]-benzamide tosylate showed improved solubility properties among other salts investigated.

Example-6

Maximum Tolerated Dose—Non-Toxic Nature

The following results (Table-3) compare the maximum tolerated dose (MTD) for 14 days of (3,5-Bis trifluoromethyl)-N-[4-methyl-3-(4-pyridin-3-yl-pyrimidin-2-ylamino)-phenyl]-benzamide tosylate to that of the basic form, (3,5-Bis trifluoromethyl)-N-[4-methyl-3-(4-pyridin-3-yl-pyrimidin-2-ylamino)-phenyl]-benzamide(base).

TABLE 3

| Sample | Species | MTD (mg/kg, po) |
|---|---|---|
| (3,5-Bis trifluoromethyl)-N-[4-methyl-3-(4-pyridin-3yl-pyrimidin-2ylamino)-phenyl]-benzamide (base) | Mice | 500.0 |
| (3,5-Bis trifluoromethyl)-N-[4-methyl-3-(4-pyridin-3yl-pyrimidin-2ylamino)-phenyl]-benzamide tosylate | Mice | 1000.0 |

The results in Table-3 show that (3,5-Bis trifluoromethyl)-N-[4-methyl-3-(4-pyridin-3-yl-pyrimidin-2-ylamino)-phenyl]-benzamide tosylate was observed to be substantially less toxic than the corresponding base, rendering the tosylate salt an unexpectedly advantageous form for the administration of this drug.

Example-7

Flow Properties

The following results (Table-4) illustrate the measured angle of repose of (3,5-Bis trifluoromethyl)-N-[4-methyl-3-(4-pyridin-3-yl-pyrimidin-2-ylamino)-phenyl]-benzamide tosylate compared to the corresponding base.

TABLE 4

| Sample | Angle of Repose (degrees °) |
|---|---|
| (3,5-Bis trifluoromethyl)-N-[4-methyl-3-(4-pyridin-3yl-pyrimidin-2ylamino)-phenyl]-benzamide (base) | 41.57 |
| (3,5-Bis trifluoromethyl)-N-[4-methyl-3-(4-pyridin-3yl-pyrimidin-2ylamino)-phenyl]-benzamide tosylate | 30.74 |

The results reported in Table-4 show that (3,5-Bis trifluoromethyl)-N-[4-methyl-3-(4-pyridin-3-yl-pyrimidin-2-ylamino)-phenyl]-benzamide tosylate exhibited a lower angle of repose and better flow properties when compared with corresponding base.

Example-8

Activity in Cell Culture

The following results (Table-5) are from a study carried out to determine the activity of (3,5-Bis trifluoromethyl)-N-[4-methyl-3-(4-pyridin-3-yl-pyrimidin-2-ylamino)-phenyl]-benzamide tosylate (AN-019T) against the corresponding base (AN-019) on K562 and T315I cell lines at $0.312 \times 10^5$ and $0.625 \times 10^5$ cells/ml respectively using dilutions of 10 μM to 0.156 μM of the test compound for 72 Hrs. Imatinib was used as standard.

TABLE 5

| Cell Line | Test Compound | $IC_{50}$ (μM) |
|---|---|---|
| K562 | Imatinib | 0.4074 |
| Chronic myelogenous | AN-019 | 0.2056 |
| leukemia (CML) | AN-019T | 0.2647 |
| T315I | Imatinib | 0.4477 |
| Chronic myelogenous | AN-019 | 0.0993 |
| leukemia (CML) | AN-019T | 0.1087 |
| Mutant | | |

CONCLUSION

By comparing the measured $IC_{50}$ values of AN-19 and AN-19T, it was concluded that AN-19 and AN-19T are comparable in inhibiting the cell proliferation of K562 and T315I. These compounds are more potent than Imatinib.

Example-9

A Formulation of the Tosylate Salt of AN-019

Table-6 (below) lists the contents of an embodiment of a formulation of (3,5-Bis trifluoromethyl)-N-[4-methyl-3-(4-pyridin-3-yl-pyrimidin-2-ylamino)-phenyl]-benzamide tosylate (AN-019T).

TABLE 6

| Components | % (w/w) |
|---|---|
| AN-019 tosylate | 57.75 |
| Sodium Lauryl Sulfate | 2.64 |
| Crospovidone | 22.18 |
| Starch 1500 | 12.15 |
| Colloidal silicon dioxide | 4.22 |
| Magnesium Stearate | 0.53 |
| Talc | 0.53 |

Example-10

Bioavailability of Tosylate Salt of AN-019

Table-7 (below) presents the results of a study that compared the bioavailability of the tosylate salt of (3,5-Bis trifluoromethyl)-N-[4-methyl-3-(4-pyridin-3-yl-pyrimidin-2-ylamino)-phenyl]-benzamide tosylate (AN-019T) to the corresponding base (AN-019) of this compound.

| Dosage form | Animal | AUC (ng hour/mL) | $T_{max}$ (hour) | $C_{max}$ (ng/mL) |
|---|---|---|---|---|
| AN-019 API | Mice | 611.46 | 6 | 93.7 |
| NRC-AN-019 Tosylate tablets | Mice | 2853.11 | 6 | 617.253 |

The above table shows that AN-019 Tosylate is more bioavailable than AN-019

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

Figures 1, 1B:
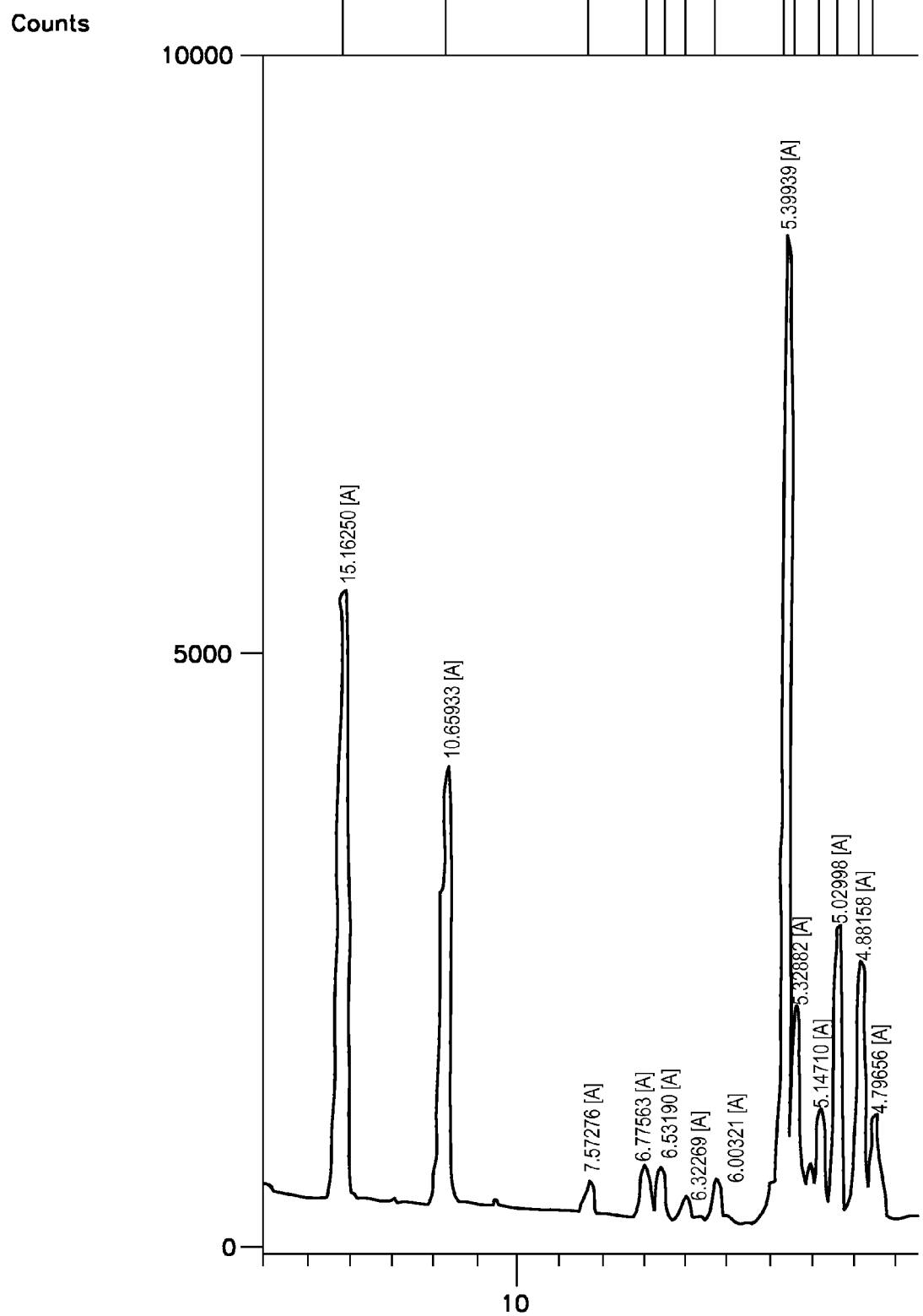
Figures 1, 1B, 2, 3:
FIG. 2 illustrates a powder X-ray diffraction (PXRD) pattern obtained for the tosylate salt of (3,5-Bis trifluoromethyl)-N-[4-methyl-3-(4-pyridin-3-yl-pyrimidin-2-ylamino)-phenyl]-benzamide.

We claim:
1. A compound of formula (II):

wherein the compound has DSC characteristics as depicted in FIG. 1 and powder x-ray diffraction (PXRD) characteristics as depicted in FIG. 2.

2. The compound of claim 1, wherein the compound remains essentially non hygroscopic at the relative humidity of 75% and at 45° C.

3. The compound of claim 1, wherein the powder x-ray diffraction (PXRD) characteristics as depicted in FIG. 2 comprise:

| Pos.[°2Th.] | Height[cts] | FWHM[°2Th.] | d-spacing[Å] | Rel.Int.[%] |
|---|---|---|---|---|
| 5.8241 | 5154.71 | 0.1560 | 15.16250 | 61.56 |
| 8.2882 | 3705.53 | 0.0936 | 10.65932 | 44.25 |
| 11.6764 | 220.10 | 0.1872 | 7.57276 | 2.63 |
| 13.0558 | 407.53 | 0.2496 | 6.77563 | 4.87 |
| 13.5452 | 432.43 | 0.1560 | 6.53190 | 5.16 |
| 13.9956 | 188.90 | 0.1872 | 6.32269 | 2.26 |
| 14.7444 | 373.73 | 0.1716 | 6.00321 | 4.46 |
| 16.4041 | 8373.23 | 0.1248 | 5.39939 | 100.00 |
| 16.6228 | 1805.88 | 0.1092 | 5.32882 | 21.57 |
| 17.2141 | 959.93 | 0.1404 | 5.14710 | 11.46 |
| 17.6181 | 2479.55 | 0.1092 | 5.02998 | 29.61 |
| 18.1581 | 2187.94 | 0.1716 | 4.88158 | 26.13 |
| 18.4828 | 906.11 | 0.1092 | 4.79656 | 10.82 |
| 20.3078 | 1497.52 | 0.1560 | 4.36944 | 17.88 |
| 20.7242 | 1704.60 | 0.1248 | 4.28256 | 20.36 |
| 21.0171 | 5927.63 | 0.0936 | 4.22355 | 70.79 |
| 22.7017 | 1808.96 | 0.1560 | 3.91380 | 21.60 |
| 23.5617 | 434.74 | 0.1560 | 3.77285 | 5.19 |
| 24.2855 | 1384.77 | 0.1560 | 3.66202 | 16.54 |
| 24.7146 | 3241.18 | 0.1092 | 3.59940 | 38.71 |
| 26.0839 | 2937.61 | 0.2496 | 3.41347 | 35.08 |
| 26.5020 | 1305.60 | 0.1716 | 3.36056 | 15.59 |
| 27.1497 | 573.99 | 0.3120 | 3.28184 | 6.86 |
| 27.7036 | 476.27 | 0.3120 | 3.21747 | 5.69 |
| 29.2557 | 979.34 | 0.1248 | 3.05020 | 11.70 |
| 31.4251 | 232.38 | 0.3744 | 2.84441 | 2.78 |
| 32.2667 | 250.22 | 0.2808 | 2.77212 | 2.99 |
| 34.6355 | 152.49 | 0.3744 | 2.58775 | 1.82 |
| 36.0878 | 397.55 | 0.1248 | 2.48687 | 4.75 |
| 37.6449 | 562.83 | 0.1248 | 2.38751 | 6.72 |
| 38.2346 | 404.70 | 0.1872 | 2.35203 | 4.83 |
| 39.7475 | 451.90 | 0.1248 | 2.26593 | 5.40 |
| 42.9248 | 367.27 | 0.3120 | 2.10527 | 4.39. |

4. A method of preparing a compound of formula (II):

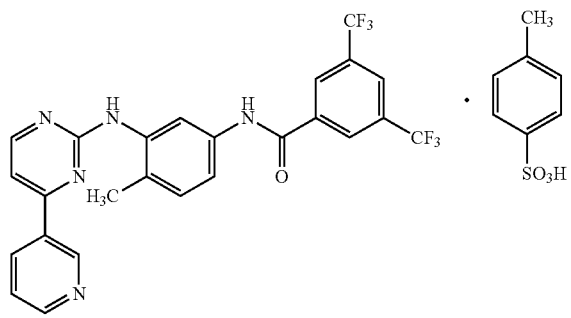 [SMILES: Cc1ccc(NC(=O)c2cc(C(F)(F)F)cc(C(F)(F)F)c2)cc1Nc1nccc(-c2cccnc2)n1 ; Cc1ccc(S(=O)(=O)O)cc1]

the method comprising treating a compound of formula (I):

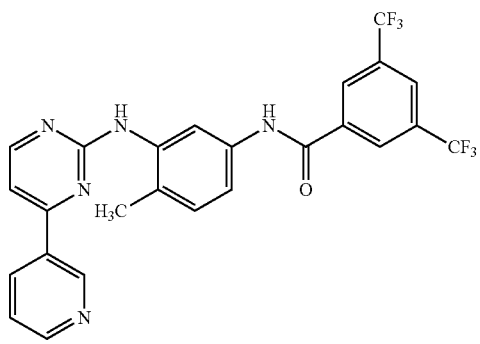 [SMILES: Cc1ccc(NC(=O)c2cc(C(F)(F)F)cc(C(F)(F)F)c2)cc1Nc1nccc(-c2cccnc2)n1]

with 4-toluene sulfonic acid in methanol at room temperature.

5. A method of treating chronic myelogenous leukemia in a subject in need thereof, comprising administering to the subject an effective amount of a compound of formula II:

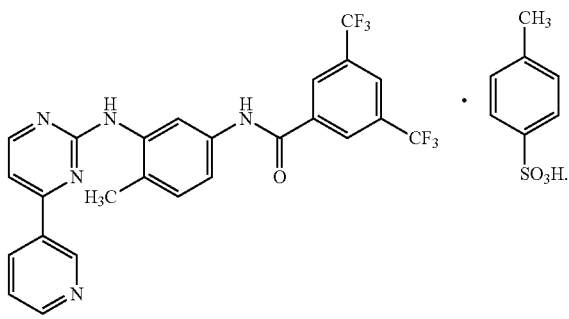 [SMILES: Cc1ccc(NC(=O)c2cc(C(F)(F)F)cc(C(F)(F)F)c2)cc1Nc1nccc(-c2cccnc2)n1 ; Cc1ccc(S(=O)(=O)O)cc1]

6. A method of treating leukemia in a subject in need thereof, the method comprising administering to the subject an effective amount of a compound of formula II:

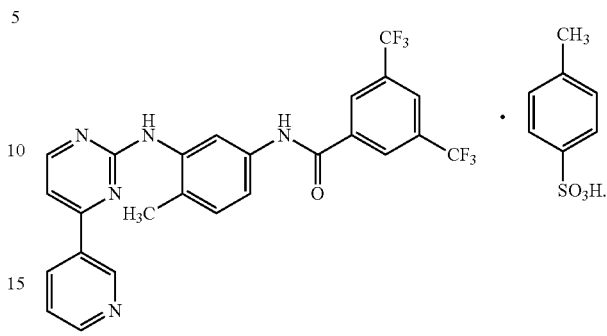

7. A salt of the compound (3,5-bis trifluoromethyl)-N-[4-methyl-3-(4-pyridin-3yl-pyrimidin-2-ylamino)-phenyl]-benzamide; wherein the salt is selected from the group consisting of hydrochloride, methane sulfonate, para-toluene sulfonate.

8. The salt of claim 7, wherein the acid addition salt is tosylate.

9. A method of treating leukemia in a subject in need thereof, comprising administering to the subject an effective amount of a salt of the compound (3,5-bis trifluoromethyl)-N-[4-methyl-3-(4-pyridin-3yl-pyrimidin-2-ylamino)-phenyl]-benzamide; wherein the salt is selected from the group consisting of hydrochloride, methane sulfonate, para-toluene sulfonate.

10. The method of claim 9, wherein the acid addition salt is tosylate.

11. The method of claim 9, wherein the leukemia comprises chronic myelogenous leukemia.

* * * * *